(12) United States Patent
Wang et al.

(10) Patent No.: US 11,963,845 B2
(45) Date of Patent: Apr. 23, 2024

(54) REGISTRATION METHOD FOR VISUAL NAVIGATION IN DENTAL IMPLANT SURGERY AND ELECTRONIC DEVICE

(71) Applicant: BEIJING YAKEBOT TECHNOLOGY CO, LTD., Beijing (CN)

(72) Inventors: Lifeng Wang, Beijing (CN); Hongpeng Liu, Beijing (CN); Chen Shen, Beijing (CN); Jianyong Ren, Beijing (CN)

(73) Assignee: BEIJING YAKEBOT TECHNOLOGY CO. LTD., Beijing (CN)

( * ) Notice: Subject to any disclaimer, the term of this patent is extended or adjusted under 35 U.S.C. 154(b) by 711 days.

(21) Appl. No.: 17/257,465

(22) PCT Filed: May 6, 2019

(86) PCT No.: PCT/CN2019/085686
§ 371 (c)(1),
(2) Date: Dec. 31, 2020

(87) PCT Pub. No.: WO2020/007111
PCT Pub. Date: Jan. 9, 2020

(65) Prior Publication Data
US 2021/0290347 A1  Sep. 23, 2021

(30) Foreign Application Priority Data
Jul. 3, 2018 (CN) .......................... 201810719110.1

(51) Int. Cl.
*A61C 9/00* (2006.01)
*A61B 34/10* (2016.01)
(Continued)

(52) U.S. Cl.
CPC .............. *A61C 9/004* (2013.01); *A61B 34/10* (2016.02); *A61C 8/00* (2013.01); *A61C 13/34* (2013.01);
(Continued)

(58) Field of Classification Search
CPC ... A61B 34/10; A61B 34/30; A61B 2034/105; A61C 9/004; A61C 8/00; A61C 13/34;
(Continued)

(56) References Cited

U.S. PATENT DOCUMENTS

2013/0337400 A1  12/2013  Yi et al.
2014/0126767 A1   5/2014  Daon et al.
2017/0367791 A1  12/2017  Raby et al.

FOREIGN PATENT DOCUMENTS

CN  101828974 A   9/2010
CN  106504331 A   3/2017
(Continued)

OTHER PUBLICATIONS

State Intellectual Property Office of the P.R. China, International Search Report dated Aug. 9, 2019 for International Application No. PCT/CN2019/085686, four pages.

(Continued)

*Primary Examiner* — Chao Sheng
(74) *Attorney, Agent, or Firm* — Dickinson Wright PLLC (57) ABSTRACT

A registration method and an electronic device for visual navigation in dental implant surgery, comprising obtaining a three-dimensional model of a target tooth to be registered, an entity model of the target tooth and a second model of the target tooth, obtaining a position and attitude matrix of the three-dimensional model in a virtual coordinate system according to the coordinates of at least three points on a three-dimensional model of a substrate after the registration of the three-dimensional model in the virtual coordinate
(Continued)

system, mounting the entity model of the target tooth onto a registration standard board, obtaining a position and attitude matrix of the entity model in the visual coordinate system according to three optical marks and the points on the entity model corresponding to the three points, and obtaining a correspondence between the virtual coordinate system and the visual coordinate system according to two position and attitude matrices.

10 Claims, 3 Drawing Sheets

(51) Int. Cl.
    *A61B 34/30*     (2016.01)
    *A61C 8/00*     (2006.01)
    *A61C 13/34*     (2006.01)
    *G06T 19/00*     (2011.01)
    *G06T 19/20*     (2011.01)

(52) U.S. Cl.
    CPC ............ *G06T 19/003* (2013.01); *G06T 19/20* (2013.01); *A61B 2034/105* (2016.02); *A61B 34/30* (2016.02); *G06T 2210/41* (2013.01); *G06T 2219/2004* (2013.01)

(58) Field of Classification Search
    CPC ... G06T 19/003; G06T 19/20; G06T 2210/41; G06T 2219/2004
    See application file for complete search history.

(56) References Cited

FOREIGN PATENT DOCUMENTS

| | | |
|---|---|---|
| CN | 107106261 A | 8/2017 |
| CN | 107230255 A | 10/2017 |
| CN | 108961326 A | 12/2018 |
| WO | 2013027577 A1 | 2/2013 |
| WO | 2018066764 A1 | 4/2018 |

OTHER PUBLICATIONS

State Intellectual Property Office of the P.R. China, International Search Report dated Aug. 9, 2019 for International Application No. PCT/CN2019/085686, two pages.

REGISTRATION METHOD FOR VISUAL NAVIGATION IN DENTAL IMPLANT SURGERY AND ELECTRONIC DEVICE

CROSS-REFERENCE TO RELATED APPLICATION

The present application is a national stage application, filed under 35 U.S.C. § 371, of International Patent Application No. PCT/CN2019/085686, filed on May 6, 2019, which application claims priority to Chinese Patent Application No. 2018107191101, filed on Jul. 3, 2018, entitled "Registration Method for Visual Navigation in Dental Implant Surgery and Electronic Device," which the disclosures of all of these applications are hereby incorporated by reference in their entireties.

FIELD OF TECHNOLOGY

The present application relates to the technical field of medical robots, and more particularly, to a registration method for visual navigation in dental implant surgery and an electronic device.

BACKGROUND

A robot has characteristics such as intelligence and high precision, which make its applications in the field of dentistry uniquely advantageous. Due to the fine and complex structure in the oral cavity, the positioning and navigation system of the robot can be needed for precise positioning to improve the treatment effect.

Before dental implantation, the doctor plans the surgical path on the three-dimensional model reconstructed based on the patient's CT image. During the surgery, a virtual space coordinate system needs to be registered with a visual coordinate system. The virtual space coordinate system is a coordinate system where the three-dimensional model of the patient's dentition reconstructed based on the CT image is located, and the visual coordinate system is a coordinate system where a robot visual navigation device is located. The landmark point registration method is often configured to register the virtual space coordinate system with the visual coordinate system, that is, the mapping relation between the two spatial coordinate systems is established by establishing the mapping relation between the landmark points in the medical image and the corresponding landmark points in the human body. The above-mentioned landmark points can be either jaw bone landmark points or dental anatomical landmark points, or small artificial landmark points. A registration method using anatomical landmark points has low registration precision, while the artificial landmark points need to be implanted into the patient's alveolar process or jaw in the registration method using artificial landmark points for registration, which will cause unnecessary trauma to the patient and even infection.

Therefore, how to propose a coordinate system registration method that can be used in robot-assisted dental implant surgery to improve the precision of the registration between coordinate systems has become an important issue to be addressed in the industry.

SUMMARY

In order to overcome at least the defects mentioned above, the present application provides a registration method for visual navigation in dental implant surgery and an electronic device.

Various embodiments include a registration method for visual navigation in dental implant surgery, including: obtaining a three-dimensional model of a target tooth to be registered and an entity model of the target tooth to be registered corresponding to the three-dimensional model of the target tooth to be registered, wherein the three-dimensional model of the target tooth to be registered includes a first three-dimensional model of a target tooth and a three-dimensional model of a substrate which are integrally connected; wherein the three-dimensional model of the substrate is preset; obtaining a second three-dimensional model of the target tooth corresponding to the first three-dimensional model of the target tooth; taking the second three-dimensional model of the target tooth as a reference and registering the three-dimensional model of the target tooth to be registered with the second three-dimensional model of the target tooth; obtaining coordinates of at least three points on the registered three-dimensional model of the substrate in a virtual coordinate system where the second three-dimensional model of the target tooth is located, and obtaining a position and attitude matrix of the three-dimensional model of the target tooth to be registered in the virtual coordinate system according to the coordinates of the at least three points in the virtual coordinate system; wherein the at least three points are preset and not collinear; mounting the entity model of the target tooth to be registered onto a prefabricated registration standard board which comprises three optical marks; obtaining coordinates of the three optical marks in the visual coordinate system, and obtaining a homogeneous matrix according to the coordinates of the three optical marks in the visual coordinate system; obtaining coordinates of points on the entity model of the target tooth to be registered corresponding to the at least three points on the three-dimensional model of the substrate in the visual coordinate system according to coordinates of the points on the entity model of the target tooth to be registered corresponding to the at least three points on the three-dimensional model of the substrate in a coordinate system of the registration standard board and the homogeneous matrix; obtaining a position and attitude matrix of the entity model of the target tooth to be registered in the visual coordinate system according to the coordinates of the points on the entity model of the target tooth to be registered corresponding to the at least three points on the three-dimensional model of the substrate in the visual coordinate system; and obtaining a correspondence between the virtual coordinate system and the visual coordinate system according to the position and attitude matrix of the three-dimensional model of the target tooth to be registered in the virtual coordinate system and the position and attitude matrix of the entity model of the target tooth to be registered in the visual coordinate system.

Other embodiments include an electronic device, comprising a processor, a memory, and a communication bus, wherein the processor and the memory communicate with each other through the communication bus; and the memory stores program instructions executable by the processor, and the processor calls the program instructions to perform the method according to the embodiments.

Additional embodiments include a non-transitory computer readable storage medium, storing computer instructions that cause a computer to perform the method according to the embodiments.

In the registration method and electronic device for visual navigation in dental implant surgery according to the present application, the three-dimensional model of the target tooth to be registered and the entity model of the target tooth to be registered corresponding to the three-dimensional model of the target tooth to be registered can be obtained, and the second three-dimensional model of the target tooth is taken as a reference to register the three-dimensional model of the target tooth to be registered with the second three-dimensional model of the target tooth; then the position and attitude matrix of the three-dimensional model of the target tooth to be registered in the virtual coordinate system is obtained according to the coordinates of at least three points on the registered three-dimensional model of the substrate in the virtual coordinate system, and the entity model of the target tooth to be registered is mounted on the prefabricated registration standard board; then the coordinates of the points on the entity model of the target tooth to be registered corresponding to the at least three points on the three-dimensional model of the substrate in the visual coordinate system are obtained according to the three optical marks and the points on the entity model of the target tooth to be registered corresponding to the at least three points on the three-dimensional model of the substrate, and the position and attitude matrix of the entity model of the target tooth to be registered in the visual coordinate system is obtained according to the coordinates of the points on the entity model of the target tooth to be registered corresponding to the at least three points on the three-dimensional model of the substrate in the visual coordinate system; and the correspondence between the virtual coordinate system and the visual coordinate system is obtained according to the above two position and attitude matrices, thereby improving the precision of registration between the coordinate systems.

BRIEF DESCRIPTION OF THE DRAWINGS

In order to more clearly illustrate the technical solutions disclosed in certain embodiments of the present application, drawings aiding in the descriptions of the embodiments are briefly described below. Obviously, the drawings in the following description are only some of the embodiments of the present application, and other drawings can be obtained according to the present disclosure without any creative effort for those skilled in the art.

DETAILED DESCRIPTION

In order to illustrate the objectives, technical solutions and advantages of the embodiments of the present application clearly, the technical solutions in certain embodiments of the present application will be described clearly and completely in conjunction with the accompanying drawings. Obviously, the described embodiments are part of the embodiments of the present application, rather than all of the embodiments. All other embodiments obtained by a person of ordinary skill in the art based on the disclosure of the present application without any creative effort fall within the protection scope of the present application.

Figure 1:
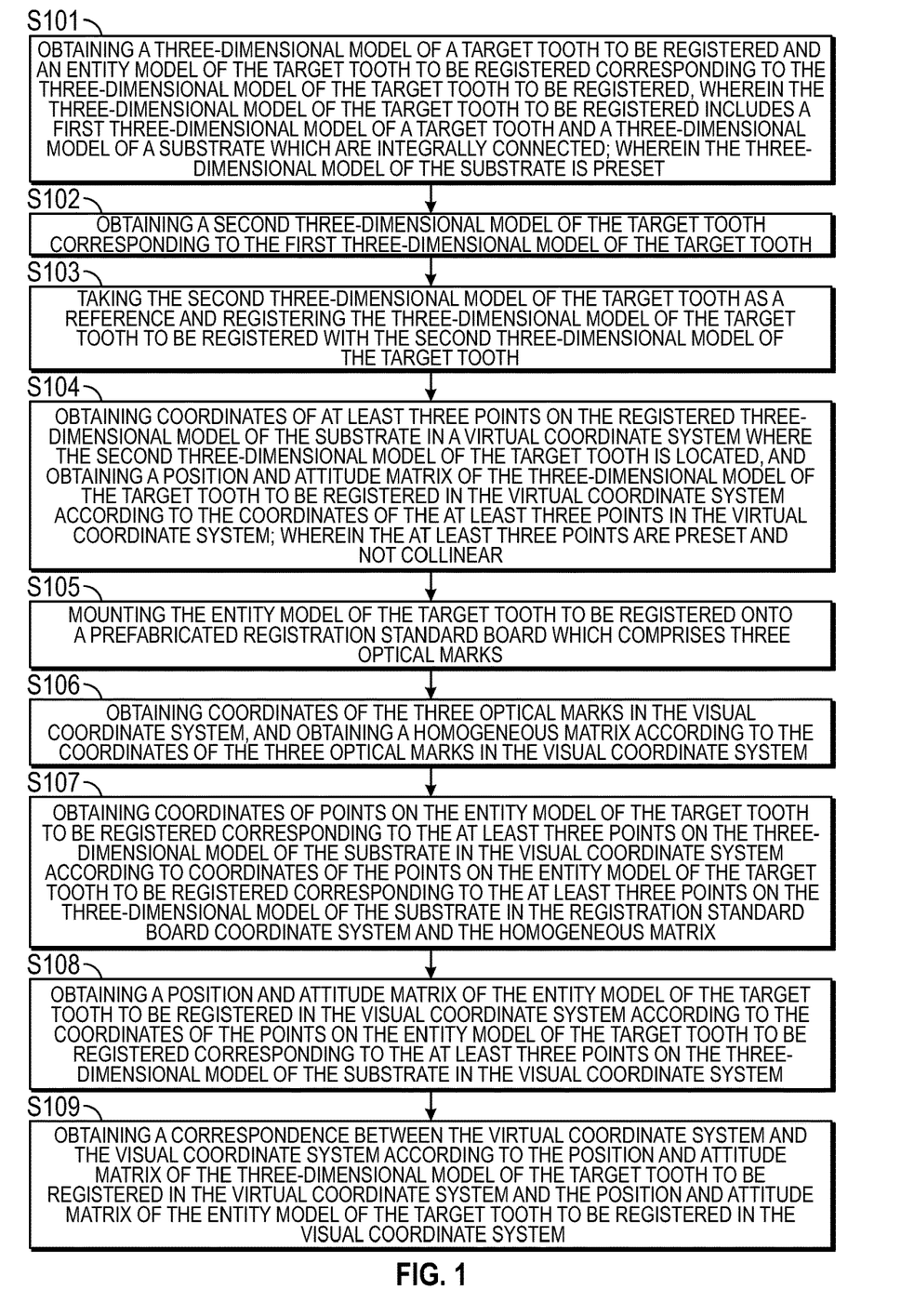
FIG. 1 is a schematic flowchart of a registration method for visual navigation in dental implant surgery according to an exemplary embodiment of the present application.

FIG. 1 is a schematic flowchart of a registration method for visual navigation in dental implant surgery according to an exemplary embodiment of the present application. As shown in FIG. 1, the registration method for visual navigation in dental implant surgery according to the present application includes the following steps.

In a step S101, obtaining a three-dimensional model of a target tooth to be registered and an entity model of the target tooth to be registered corresponding to the three-dimensional model of the target tooth to be registered, wherein the three-dimensional model of the target tooth to be registered includes a first three-dimensional model of a target tooth and a three-dimensional model of a substrate which are integrally connected; wherein the three-dimensional model of the substrate is preset.

Specifically, a three-dimensional model of a target tooth to be registered and an entity model of the target tooth to be registered corresponding to the three-dimensional model of the target tooth to be registered are obtained, where the entity model of the target tooth to be registered can be printed and produced by a 3D printer according to the three-dimensional model of the target tooth to be registered. The three-dimensional model of the target tooth to be registered includes a first three-dimensional model of a target tooth and a three-dimensional model of a substrate, the first three-dimensional model of the target tooth is the object of dental implant surgery, and may be a three-dimensional model of the lower tooth or a three-dimensional model of the upper teeth of a patient. The three-dimensional model of the substrate is preset, and the registration of visual navigation in implant surgery is provided by introducing the three-dimensional model of the substrate.

For example, a patient's tooth model can be made using methods of making impressions and reproducing plaster models in stomatology, and then a bin scanner may be used to scan and obtain the three-dimensional model of the patient's tooth, thereby obtaining the first three-dimensional model of the target tooth. A hand-held digital intraoral scanner can also be used to directly scan the patient's oral cavity to directly obtain the three-dimensional model of the patient's tooth, thereby obtaining the first three-dimensional model of the target tooth. Then, the first three-dimensional model of the target tooth and the three-dimensional model of the substrate may be integrated into one body to form the three-dimensional model of the target tooth to be registered.

In a step S102, obtaining a second three-dimensional model of the target tooth corresponding to the first three-dimensional model of the target tooth.

Specifically, a cone beam computed tomography (referred to as CBCT) scanning may be performed on the patient, and a Marching cubes algorithm may be used to perform three-dimensional reconstruction on a series of two-dimensional CT images obtained from the scanning to obtain a second three-dimensional model of the target tooth of the patient. The second three-dimensional model of the target tooth corresponds to the first three-dimensional model of the target tooth, for example, when the first three-dimensional model of the target tooth is a three-dimensional model of a lower tooth, the second three-dimensional model of the target tooth is also the three-dimensional model of the lower tooth.

In a step S103, taking the second three-dimensional model of the target tooth as a reference and registering the three-dimensional model of the target tooth to be registered with the second three-dimensional model of the target tooth.

Specifically, the three-dimensional registration model of the target tooth is imported into the three-dimensional space where the second three-dimensional model of the target tooth is located, and then the second three-dimensional model of the target tooth is taken as a reference to make the first three-dimensional model of the target tooth included in the three-dimensional model of the target tooth coincide with the second three-dimensional model of the target tooth, so that the three-dimensional model of the target tooth to be registered is registered with the second three-dimensional model of the target tooth.

For example, four points are acquired on the second three-dimensional model of the target tooth, and points corresponding to the four points on the second three-dimensional model of the target tooth are acquired on the first three-dimensional model of the target tooth. The second three-dimensional model of the target tooth and the three-dimensional model of the target tooth to be registered are roughly registered according to the above four pairs of corresponding points. When the distance between each pair of corresponding points is within a preset error range, the rough registration is completed. After the rough registration, an ICP algorithm may be used to finely register the second three-dimensional model of the target tooth with the three-dimensional model of the target tooth to be registered. During the fine registration, it may be necessary to set parameters of the ICP algorithm, such as the number of sampling points, the target mean square error, the maximum number of iterations, etc., to perform the calculation of the fine registration, where the preset error and the parameters of the ICP algorithm are set according to actual experience.

In a step S104, obtaining coordinates of at least three points on the registered three-dimensional model of the substrate in a virtual coordinate system where the second three-dimensional model of the target tooth is located, and obtaining a position and attitude matrix of the three-dimensional model of the target tooth to be registered in the virtual coordinate system according to the coordinates of the at least three points in the virtual coordinate system; wherein the at least three points are preset and not collinear.

Specifically, after the three-dimensional model of the target tooth is registered completely with the second three-dimensional model of the target tooth, the coordinates of at least three points on the three-dimensional model of the substrate in the virtual coordinate system where the second three-dimensional model of the target tooth is located can be obtained. Then, the position and attitude matrix of the three-dimensional model of the target tooth to be registered in the virtual coordinate system can be obtained according to the coordinates of the at least three points.

In a step S105, mounting the entity model of the target tooth to be registered onto a prefabricated registration standard board which comprises three optical marks.

Specifically, the entity model of the target tooth to be registered is mounted onto a registration standard board, which is prefabricated and comprises three optical marks capable of reflecting infrared light. The positions of the three optical marks on the registration standard board are set according to actual experience.

Figure 2:
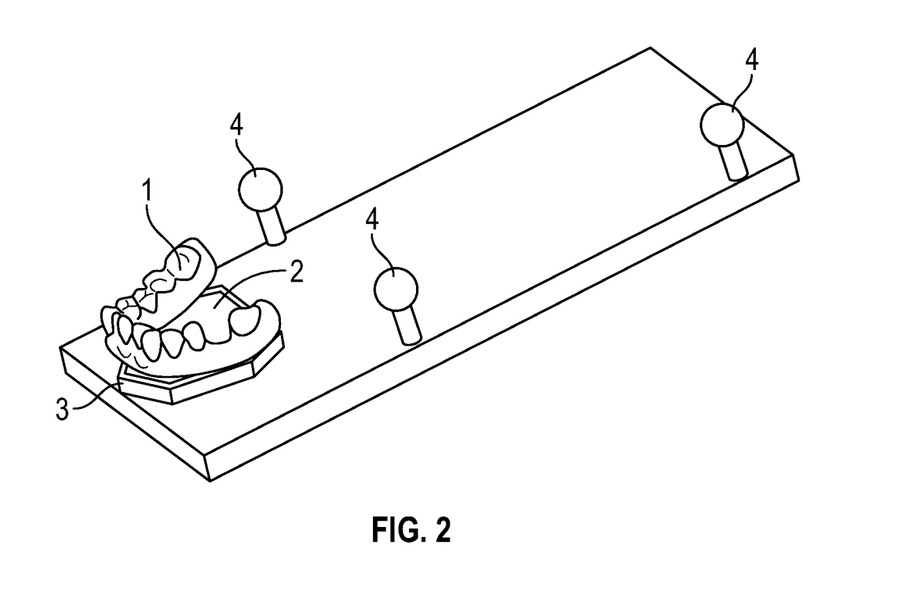
FIG. 2 is a schematic diagram of an assembly structure of an entity model of a target tooth to be registered and a registration standard board according to an exemplary embodiment of the present application.

For example, FIG. 2 is a schematic diagram of an assembly structure of an entity model of the target tooth to be registered and the registration standard board according to an exemplary embodiment of the present application. As shown in FIG. 2, the registration standard board includes optical marks 4 and a mounting groove 3, and the entity model of the target tooth to be registered includes an entity model of the substrate 2 and a first entity model of the target tooth 1. The entity model of the substrate 2 corresponds to the mounting groove 3, and during installation, the entity model of the substrate 2 is assembled into the mounting groove 3 to mount the entity model of the target tooth to be registered onto the registration standard board. The positions of the optical marks 4 and the mounting groove 3 on the registration standard board are set according to actual needs.

In a step S106, obtaining coordinates of the three optical marks in the visual coordinate system, and obtaining a homogeneous matrix according to the coordinates of the three optical marks in the visual coordinate system.

Specifically, the coordinates of the three optical marks in the visual coordinate system can be obtained by using a camera of a robot visual navigation device to photograph the three optical marks, and the homogeneous matrix can be obtained according to the coordinates of each optical mark. The homogeneous matrix can be used to transform the coordinates in the registration standard board coordinate system into the coordinates in the visual coordinate system, wherein the visual coordinate system is the coordinate system of the robot visual navigation device, and the registration standard board coordinate system is preset.

In a step S107, obtaining coordinates of points on the entity model of the target tooth to be registered corresponding to the at least three points on the three-dimensional model of the substrate in the visual coordinate system according to coordinates of the points on the entity model of the target tooth to be registered corresponding to the at least three points on the three-dimensional model of the substrate in the registration standard board coordinate system and the homogeneous matrix.

Specifically, the entity model of the target tooth to be registered includes an entity model of the substrate, on which there are points (hereinafter referred to as corresponding points) corresponding to the at least three points on the three-dimensional model of the substrate. The coordinate system in which the registration standard board is designed can be used as the registration standard board coordinate system, and the coordinates of any position on the registration standard board in the registration standard board coordinate system can be obtained. After the entity model of the target tooth to be registered is mounted on the prefabricated registration standard board, the coordinates of the corresponding points in the registration standard board coordinate system can be obtained, and the coordinates of each corresponding point in the visual coordinate system can be obtained by multiplying the coordinates of each corresponding point in the registration standard board coordinate system by the homogeneous matrix. It is understood that an assembly error between the registration standard board and the entity model of the target tooth to be registered may be negligibly small.

For example, when the registration standard board is designed, a number of reference points which correspond to the corresponding points one-to-one are set. The coordinates of the reference points in the registration standard board coordinate system are known, and the reference point may be a point that coincides with the corresponding point after the entity model of the target tooth to be registered is mounted on the registration standard board, or it may be a point whose relative coordinates to the corresponding point are known. After the entity model of the target tooth to be registered is mounted on the registration standard board, when the reference point coincides with the corresponding point, then the coordinates of the reference point in the registration standard board coordinate system are the coordinates of the corresponding point in the registration standard board coordinate system; when the reference point does not coincide with the corresponding point, then the coordinates of the corresponding point in the registration standard board coordinate system can be obtained according to the coordinates of the reference point in the registration standard board coordinate system and the relative coordinates between the reference point and the corresponding point.

In a step S108, obtaining a position and attitude matrix of the entity model of the target tooth to be registered in the visual coordinate system according to the coordinates of the points on the entity model of the target tooth to be registered corresponding to the at least three points on the three-dimensional model of the substrate in the visual coordinate system.

Specifically, after obtaining the coordinates of each corresponding point in the visual coordinate system, the position and attitude matrix of the entity model of the target tooth to be registered in the visual coordinate system can be obtained according to the coordinates of each corresponding point in the visual coordinate system.

In a step S109, obtaining a correspondence between the virtual coordinate system and the visual coordinate system according to the position and attitude matrix of the three-dimensional model of the target tooth to be registered in the virtual coordinate system and the position and attitude matrix of the entity model of the target tooth to be registered in the visual coordinate system.

Specifically, after obtaining the position and attitude matrix $T_1$ of the three-dimensional model of the target tooth to be registered in the virtual coordinate system, and the position and attitude matrix $T_2$ of the entity model of the target tooth to be registered in the visual coordinate system, the transformation matrix between the virtual coordinate system and the visual coordinate system can be obtained by multiplying the inverse matrices of $T_1$ and $T_2$, that is, the correspondence between the virtual coordinate system and the visual coordinate system can be obtained. By means of the above transformation matrix, the coordinates of each position in the virtual coordinate system and in the visual coordinate system can be unified into coordinates in one coordinate system, and the coordinates of the corresponding point on the entity model of the target tooth corresponding to the first three-dimensional model of the target tooth in the visual coordinate system can be obtained through the transformation matrix according to the coordinates of a point on the first three-dimensional model of the target tooth in the virtual coordinate system, thereby using virtual environment to guide dental implant surgery in realistic environment.

In the registration method and electronic device for visual navigation in dental implant surgery according to the present application, the three-dimensional model of the target tooth to be registered and the entity model of the target tooth to be registered corresponding to the three-dimensional model of the target tooth to be registered can be obtained, and the second three-dimensional model of the target tooth is taken as a reference to register the three-dimensional model of the target tooth to be registered with the second three-dimensional model of the target tooth; then the position and attitude matrix of the three-dimensional model of the target tooth to be registered in the virtual coordinate system is obtained according to the coordinates of at least three points on the registered three-dimensional model of the substrate in the virtual coordinate system, and the entity model of the target tooth to be registered is mounted on the prefabricated registration standard board; then the coordinates of the points on the entity model of the target tooth to be registered corresponding to the at least three points on the three-dimensional model of the substrate in the visual coordinate system are obtained according to the three optical marks and the points on the entity model of the target tooth to be registered corresponding to the at least three points on the three-dimensional model of the substrate, and the position and attitude matrix of the entity model of the target tooth to be registered in the visual coordinate system is obtained according to the coordinates of the points on the entity model of the target tooth to be registered corresponding to the at least three points on the three-dimensional model of the substrate in the visual coordinate system; finally, the correspondence between the virtual coordinate system and the visual coordinate system is obtained according to the above two position and attitude matrices, thereby improving the precision of registration between the coordinate systems.

Figure 3:
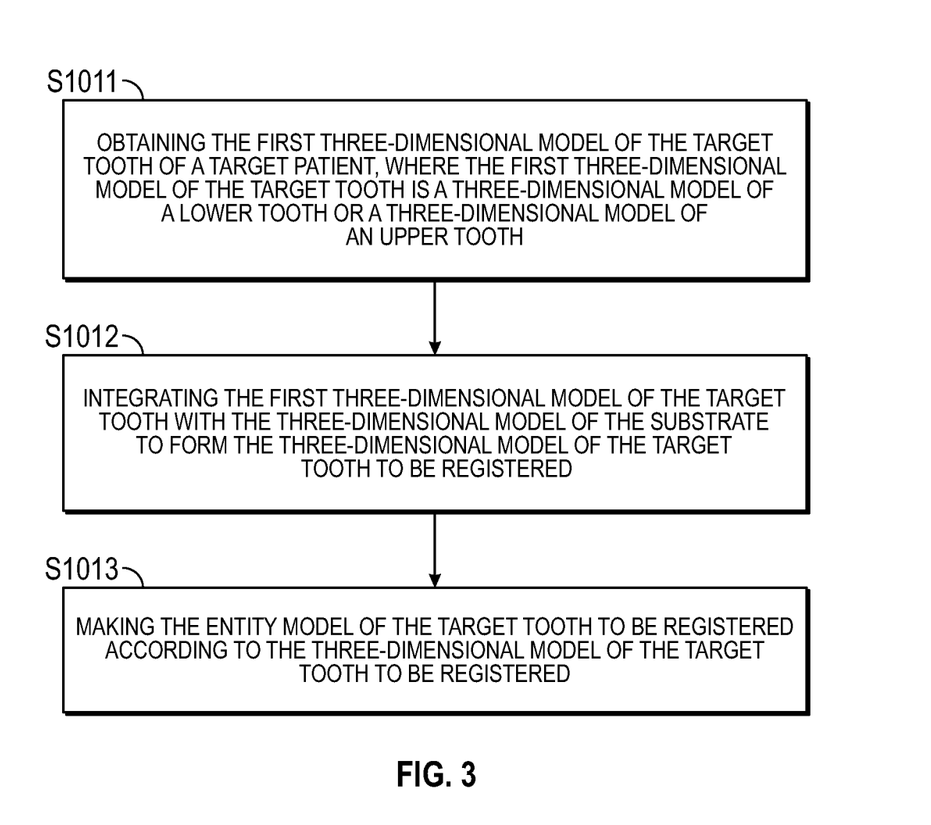
FIG. 3 is a schematic flowchart of a registration method for visual navigation in dental implant surgery according to another exemplary embodiment of the present application.

FIG. 3 is a schematic flowchart of a registration method for visual navigation in dental implant surgery according to another exemplary embodiment of the present application. As shown in FIG. 3, the obtaining of a three-dimensional model of a target tooth to be registered and an entity model of the target tooth to be registered corresponding to the three-dimensional model of the target tooth to be registered includes the following steps.

In a step S1011, obtaining a first three-dimensional model of the target tooth of a target patient, where the first three-dimensional model of the target tooth is a three-dimensional model of a lower tooth or a three-dimensional model of an upper tooth.

Specifically, methods of making impressions and reproducing plaster models in stomatology can be used to make a patient's tooth model, and then a bin scanner may be used to scan and obtain the three-dimensional model of the patient's tooth, thereby obtaining the first three-dimensional model of the target tooth. A hand-held digital intraoral scanner can also be used to directly scan the patient's oral cavity to directly obtain the three-dimensional model of the patient's tooth, thereby obtaining the first three-dimensional model of the target tooth.

In a step S1012, integrating the first three-dimensional model of the target tooth with a three-dimensional model of a substrate to form the three-dimensional model of the target tooth to be registered.

Specifically, the first three-dimensional model of the target tooth may be disposed on the three-dimensional model of the substrate and contacted therewith, and then the first three-dimensional model of the target tooth and the three-dimensional model of the substrate may be connected into a whole through, for example, a Boolean addition operation, thereby forming the three-dimensional model of the target tooth to be registered.

In a step S1013, making the entity model of the target tooth to be registered according to the three-dimensional model of the target tooth to be registered.

Specifically, using a 3D printer to print out the three-dimensional model of the target tooth to be registered to obtain the entity model of the target tooth to be registered. The entity model of the target tooth to be registered includes a first entity model of the target tooth corresponding to the first three-dimensional model of the target tooth and an entity model of the substrate corresponding to the three-dimensional model of the substrate.

According to an exemplary embodiment, the three-dimensional model of the substrate is a polyhedral three-dimensional model with a regular shape.

Specifically, the three-dimensional model of the substrate is a regular-shaped polyhedral three-dimensional model, and the corresponding entity model of the substrate is a regular-shaped polyhedral entity model, thereby facilitating the installation. The term regular shape may be defined as, for example, a polyhedral three-dimensional model that is a polygonal and has a surface thereof that is flat. The specific shape of the polyhedral three-dimensional model may be set according to actual needs.

According to an exemplary embodiment, the at least three points are vertices of the polyhedral three-dimensional model.

Specifically, when providing the at least three points, the vertices of the polyhedral three-dimensional model may be selected. If the at least three points are four points, the four vertices of the polyhedral three-dimensional model can be set as the four points, thereby facilitating the acquisition of coordinates of them and the acquisition of the coordinates of the corresponding points in the registration standard board coordinate system.

According to an exemplary embodiment, an entity model of the substrate is a polyhedral physical model with a regular shape, and the registration standard board includes an assembly groove corresponding to a polyhedral entity model; wherein mounting the entity model of the target tooth to be registered onto a prefabricated registration standard board includes assembling the polyhedral entity model into the assembly groove.

Figure 4:
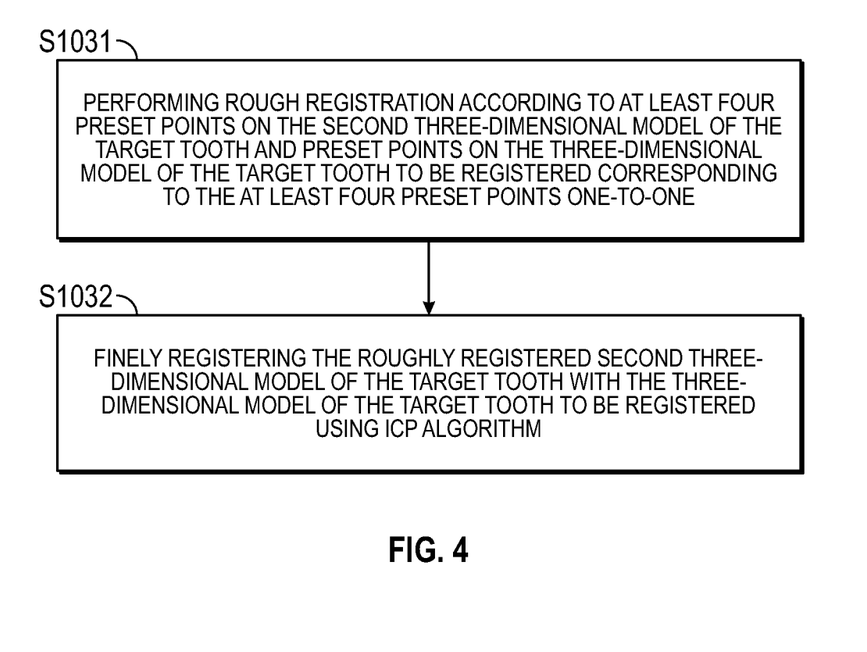
FIG. 4 is a schematic flowchart of a registration method for visual navigation in dental implant surgery according to yet another exemplary embodiment of the present application.

FIG. 4 is a schematic flowchart of a registration method for visual navigation in dental implant surgery according to yet another exemplary embodiment of the present application. As shown in FIG. 4, the taking of a second three-dimensional model of the target tooth as a reference and registering the three-dimensional model of the target tooth to be registered with the second three-dimensional model of the target tooth include the following steps.

In a step S1031, performing rough registration according to at least four preset points on the second three-dimensional model of the target tooth and to preset points on the three-dimensional model of the target tooth to be registered corresponding on a one-to-one basis to the at least four preset points.

Specifically, at least four preset points are acquired on the second three-dimensional model of the target tooth, and the preset points corresponding on a one-to-one basis to four preset points on the second three-dimensional model of the target tooth are obtained on the first three-dimensional model of the target tooth. Rough registration is performed on the second three-dimensional model of the target tooth and the three-dimensional model of the target tooth to be registered according to the aforementioned at least four pairs of corresponding points, and when the distance between each pair of corresponding points is within a preset error range, the rough registration is complete. The preset points may be set based on actual experience. Further, the preset error range may also be set based on actual experience.

In a step S1032, finely registering the roughly registered second three-dimensional model of the target tooth with the three-dimensional model of the target tooth to be registered using, for example, an ICP algorithm.

Specifically, after rough registration, the second three-dimensional model of the target tooth may be finely registered with the three-dimensional model of the target tooth to be registered using the ICP algorithm. During the fine registration, it is necessary to set the parameters of the ICP algorithm, such as the number of sampling points, the target mean square error, the maximum number of iterations, etc., to perform the calculation of the fine registration. The parameters of the ICP algorithm may be set according to actual experience.

According to an exemplary embodiment, the obtaining a correspondence between the virtual coordinate system and the visual coordinate system according to the position and attitude matrix of the three-dimensional model of the target tooth to be registered in the virtual coordinate system and the position and attitude matrix of the entity model of the target tooth to be registered in the visual coordinate system may include the following steps.

Obtaining a transformation matrix $T_0$ between the virtual coordinate system and the visual coordinate system according to, for example, the equation $T_0=T_1 \cdot (T_2)^{-1}$, wherein $T_1$ is the position and attitude matrix of the three-dimensional model of the target tooth to be registered in the virtual coordinate system, and $T_2$ is the position and attitude matrix of the entity model of the target tooth to be registered in the visual coordinate system.

Specifically, after the position and attitude matrix $T_1$ of the three-dimensional model of the target tooth to be registered in the virtual coordinate system and the position and attitude matrix $T_2$ of the entity model of the target tooth to be registered in the visual coordinate system are obtained, the transformation matrix $T_0$ between the virtual coordinate system and the visual coordinate system can be calculated according to the equation $T_0=T_1 \cdot (T_2)^{-1}$.

According to an exemplary embodiment, a plurality of the entity models of the target tooth to be registered are mounted on the registration standard board.

Specifically, a plurality of mounting positions of the entity model of the target tooth to be registered can be set on the registration standard board, and a plurality of the entity model of the target tooth to be registered can be mounted at a time, which improves the efficiency of registration.

Figure 5:
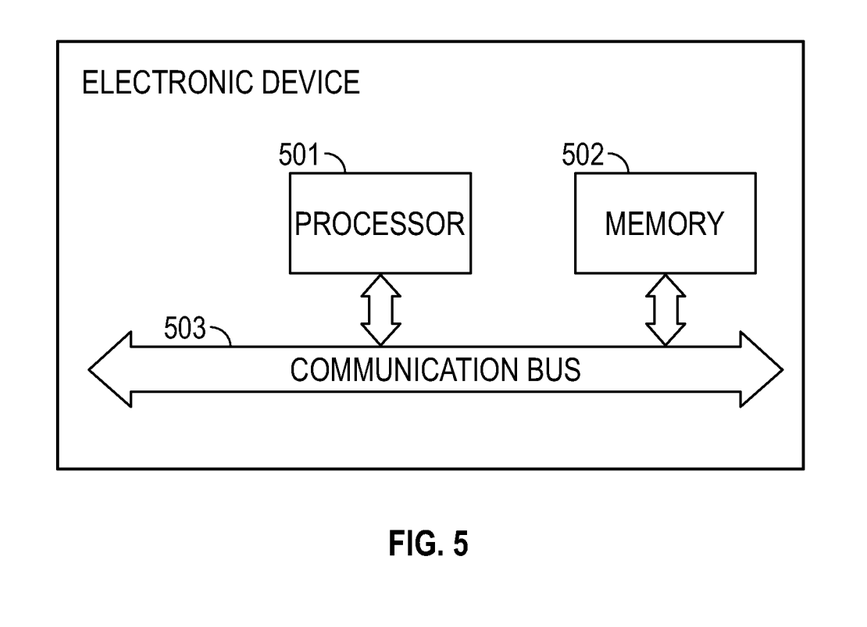
FIG. 5 is a schematic diagram of a physical structure of an electronic device according to an exemplary embodiment of the present application.

FIG. 5 is a schematic diagram of a physical structure of an electronic device according to an exemplary embodiment of the present application.

As shown in FIG. 5, the electronic device includes a processor 501, a memory 502 and a communication bus 503.

The processor 501 and the memory 502 communicate with each other through the communication bus 503.

The processor 501 may be configured to call program instructions in the memory 502 to perform the methods according to the foregoing method embodiments, for example, including: obtaining a three-dimensional model of a target tooth to be registered and an entity model of the target tooth to be registered corresponding to the three-dimensional model of the target tooth to be registered, where the three-dimensional model of the target tooth to be registered includes a first three-dimensional model of a target tooth and a three-dimensional model of a substrate which are integrally connected; where the three-dimensional model of the substrate is preset; obtaining a second three-dimensional model of the target tooth corresponding to the first three-dimensional model of the target tooth; taking the second three-dimensional model of the target tooth as a reference and registering the three-dimensional model of the target tooth to be registered with the second three-dimensional model of the target tooth; obtaining coordinates of at least three points on the registered three-dimensional model of the substrate in a virtual coordinate system where the second three-dimensional model of the target tooth is located, and obtaining a position and attitude matrix of the three-dimensional model of the target tooth to be registered in the virtual coordinate system according to the coordinates of the at least three points in the virtual coordinate system; wherein the at least three points are preset and not collinear; mounting the entity model of the target tooth to be registered onto a prefabricated registration standard board which comprises three optical marks; obtaining coordinates of the three optical marks in the visual coordinate system, and obtaining a homogeneous matrix according to the coordinates of the three optical marks in the visual coordinate system; obtaining coordinates of points on the entity model of the target tooth to be registered corresponding to the at least three points on the three-dimensional model of the substrate in the visual coordinate system according to coordinates of the points on the entity model of the target tooth to be registered corresponding to the at least three points on the three-dimensional model of the substrate in the registration standard board coordinate system and the homogeneous matrix; obtaining a position and attitude matrix of the entity model of the target tooth to be registered in the visual coordinate system according to the coordinates of the points on the entity model of the target tooth to be registered in the visual coordinate system corresponding to the at least three points on the three-dimensional model of the substrate; and obtaining a correspondence between the virtual coordinate system and the visual coordinate system according to the position and attitude matrix of the three-dimensional model of the target tooth to be registered in the virtual coordinate system and the position and attitude matrix of the entity model of the target tooth to be registered in the visual coordinate system.

Further exemplary embodiments provide a computer program product, including a computer program stored on a non-transitory computer readable storage medium, where the computer program includes program instructions, and the computer can perform, when performing the program instructions, the methods according to the foregoing method embodiments, for example, including: obtaining a three-dimensional model of a target tooth to be registered and an entity model of the target tooth to be registered corresponding to the three-dimensional model of the target tooth to be registered, wherein the three-dimensional model of the target tooth to be registered includes a first three-dimensional model of a target tooth and a three-dimensional model of a substrate which are integrally connected; wherein the three-dimensional model of the substrate is preset; obtaining a second three-dimensional model of a target tooth corresponding to the first three-dimensional model of the target tooth; taking the second three-dimensional model of the target tooth as a reference and registering the three-dimensional model of the target tooth to be registered with the second three-dimensional model of the target tooth; obtaining coordinates of at least three points on the registered three-dimensional model of the substrate in a virtual coordinate system where the second three-dimensional model of the target tooth is located, and obtaining a position and attitude matrix of the three-dimensional model of the target tooth to be registered in the virtual coordinate system according to the coordinates of the at least three points in the virtual coordinate system; wherein the at least three points are preset and not collinear; mounting the entity model of the target tooth to be registered onto a prefabricated registration standard board which comprises three optical marks; obtaining coordinates of the three optical marks in the visual coordinate system, and obtaining a homogeneous matrix according to the coordinates of the three optical marks in the visual coordinate system; obtaining coordinates of points on the entity model of the target tooth to be registered corresponding to the at least three points on the three-dimensional model of the substrate in the visual coordinate system according to coordinates of the points on the entity model of the target tooth to be registered corresponding to the at least three points on the three-dimensional model of the substrate in the registration standard board coordinate system and the homogeneous matrix; obtaining a position and attitude matrix of the entity model of the target tooth to be registered in the visual coordinate system according to the coordinates of the points on the entity model of the target tooth to be registered corresponding to the at least three points on the three-dimensional model of the substrate in the visual coordinate system; and obtaining a correspondence between the virtual coordinate system and the visual coordinate system according to the position and attitude matrix of the three-dimensional model of the target tooth to be registered in the virtual coordinate system and the position and attitude matrix of the entity model of the target tooth to be registered in the visual coordinate system.

Additional exemplary embodiments provide a non-transitory computer readable storage medium, storing computer instructions that cause a computer to perform the methods according to the foregoing method embodiments, for example, including: obtaining a three-dimensional model of a target tooth to be registered and an entity model of the target tooth to be registered corresponding to the three-dimensional model of the target tooth to be registered, wherein the three-dimensional model of the target tooth to be registered includes a first three-dimensional model of a target tooth and a three-dimensional model of a substrate which are integrally connected; wherein the three-dimensional model of the substrate is preset; obtaining a second three-dimensional model of a target tooth corresponding to the first three-dimensional model of the target tooth; taking the second three-dimensional model of the target tooth as a reference and registering the three-dimensional model of the target tooth to be registered with the second three-dimensional model of the target tooth; obtaining coordinates of at least three points on the registered three-dimensional model of the substrate in a virtual coordinate system where the second three-dimensional model of the target tooth is located, and obtaining a position and attitude matrix of the three-dimensional model of the target tooth to be registered in the virtual coordinate system according to the coordinates of the at least three points in the virtual coordinate system; where the at least three points are preset and not collinear; mounting the entity model of the target tooth to be registered onto a prefabricated registration standard board which comprises three optical marks; obtaining coordinates of the three optical marks in the visual coordinate system, and obtaining a homogeneous matrix according to the coordinates of the three optical marks in the visual coordinate system; obtaining coordinates of points on the entity model of the target tooth to be registered corresponding to the at least three points on the three-dimensional model of the substrate in the visual coordinate system according to coordinates of the points on the entity model of the target tooth to be registered corresponding to the at least three points on the three-dimensional model of the substrate; obtaining a position and attitude matrix of the entity model of the target tooth to be registered in the visual coordinate system according to the coordinates of the points on the entity model of the target tooth to be registered in the visual coordinate system corresponding to the at least three points on the three-dimensional model of the substrate; and obtaining a correspondence between the virtual coordinate system and the visual coordinate system according to the position and attitude matrix of the three-dimensional model of the target tooth to be registered in the virtual coordinate system and the position and attitude matrix of the entity model of the target tooth to be registered in the visual coordinate system.

In addition, the logic instructions in the memory described above may be implemented in the form of a software functional unit and may be stored in a computer readable storage medium while being sold or used as a separate product. Based on such understanding, the technical solution of the present application, or a part of the technical solution, may be embodied in the form of a software product, which is stored in a storage medium, including several instructions to cause a computer device (which may be a personal computer, server, or network device, etc.) to perform all or part of the steps of the methods described in various embodiments of the present application. The storage medium described above may comprise: a U disk, a mobile hard disk, a read-only memory (ROM), a random access memory (RAM), a magnetic disk, a compact disk, and the like.

Through the description of the exemplary embodiments above, those skilled in the art can clearly understand that the various embodiments can be implemented by means of software and a hardware platform, and of course, by hardware. Based on such understanding, the technical solution of the present application, or a part of the technical solution, may be embodied in the form of a software product, which is stored in a storage medium such as ROM/RAM, magnetic discs, compact discs, etc., including several instructions to cause a computer device (for example, a personal computer, server, or network device, etc.) to perform the methods described in various embodiments or part of the embodiments.

It should be noted that the above-described exemplary embodiments are only for illustrating the technical solutions of the present application, rather than limiting them; although the present application has been described in detail with reference to the foregoing embodiments, those skilled in the art should understand that the technical solutions documented in the preceding embodiments may still be modified, or parts of the technical features thereof can be equivalently substituted; and such modifications or substitutions do not deviate from the spirit and scope of the technical solutions of the embodiments of the present application.

The invention claimed is:

1. A method for performing visual navigation assisted dental implant surgery, the method comprising, by a computing device:
   obtaining a baseline 3D model of a target tooth to be registered, wherein the baseline 3D model includes (1) a first 3D model of an entity model of the target tooth, and a (2) 3D model of a substrate to which the entity model is attached, wherein the 3D model of the substrate is preset;
   performing a live scan of the target tooth to obtain a second 3D model that corresponds to the first 3D model;
   utilizing the second 3D model as a reference to register the baseline 3D model with the second 3D model;
   obtaining coordinates of at least three points on the 3D model of the substrate in a virtual coordinate system in which the second 3D model is located, and obtaining a position and attitude matrix of the baseline 3D model in the virtual coordinate system according to the coordinates of the at least three points in the virtual coordinate system, wherein the at least three points are preset and not collinear;
   obtaining, by imaging a prefabricated registration standard board that comprises three optical marks, and onto which the entity model is mounted, coordinates of the three optical marks in a visual coordinate system, and obtaining a homogeneous matrix according to the coordinates of the three optical marks in the visual coordinate system;
   obtaining coordinates of points on the entity model corresponding to the at least three points on the 3D model of the substrate in the visual coordinate system according to coordinates of the points on the entity model corresponding to the at least three points on the 3D model of the substrate in the prefabricated registration standard board and the homogeneous matrix;
   obtaining a position and attitude matrix of the entity model in the visual coordinate system according to the coordinates of the points on the entity model corresponding to the at least three points on the 3D model of the substrate in the visual coordinate system;
   obtaining a correspondence between the virtual coordinate system and the visual coordinate system according to the position and attitude matrix of the baseline 3D model in the virtual coordinate system and the position and attitude matrix of the entity model in the visual coordinate system; and
   providing the correspondence to a navigation device to enable robot-assisted dental implant surgery to be performed on the target tooth.

2. The method of claim 1, wherein the obtaining the baseline 3D model comprises:
   obtaining the first 3D model of the target tooth of a target patient, wherein the first 3D model of the target tooth is a 3D model of a lower tooth or a 3D model of an upper tooth;
   integrating the first 3D model of the target tooth with the 3D model of the substrate to form the baseline 3D model.

3. The method of claim 1, wherein utilizing the second 3D model as a reference to register the baseline 3D model with the second 3D model comprises:
   performing a rough registration according to at least four preset points on the second 3D model and preset points on the baseline 3D model corresponding on a one-to-one basis to the at least four preset points; and
   finely registering the roughly registered second 3D model with the baseline 3D model using an ICP algorithm.

4. The method of claim 1, wherein obtaining the correspondence between the virtual coordinate system and the visual coordinate system according to the position and attitude matrix of the baseline 3D model in the virtual coordinate system and the position and attitude matrix of the entity model in the visual coordinate system comprises:
   obtaining a transformation matrix, $T_0$, between the virtual coordinate system and the visual coordinate system according to the equation, $T_0=T_1 \cdot (T_2)^{-1}$, wherein $T_1$ is the position and attitude matrix of the baseline 3D model in the virtual coordinate system, and $T_2$ is the position and attitude matrix of the entity model in the visual coordinate system.

5. The method of claim 1, wherein at least one additional entity model of the target tooth is mounted on the prefabricated registration standard board.

6. The method of claim 1, wherein the 3D model of the substrate is a polyhedral 3D model with a regular shape.

7. The method of claim 6, wherein the at least three points are vertices of the polyhedral 3D model.

8. The method of claim 6, wherein:
an entity model of the substrate is a polyhedral physical model with a regular shape, and the prefabricated registration standard board includes an assembly groove that corresponds to the polyhedral physical model; and
the entity model of the substrate is mounted onto the prefabricated registration standard board by way of assembling the polyhedral physical model into the assembly groove.

9. An electronic device, comprising:
at least one processor, at least one memory, and at least one communication bus, wherein:
the at least one processor and the at least one memory communicate with each other through the at least one communication bus; and
the at least one memory stores program instructions executable by the at least one processor, and the at least one processor calls the program instructions to carry out steps that include:
obtaining a baseline 3D model of a target tooth to be registered, wherein the baseline 3D model includes (1) a first 3D model of an entity model of the target tooth, and a (2) 3D model of a substrate to which the entity model is attached, wherein the 3D model of the substrate is preset;
performing a live scan of the target tooth to obtain a second 3D model that corresponds to the first 3D model;
utilizing the second 3D model as a reference to register the baseline 3D model with the second 3D model;
obtaining coordinates of at least three points on the 3D model of the substrate in a virtual coordinate system in which the second 3D model is located, and obtaining a position and attitude matrix of the baseline 3D model in the virtual coordinate system according to the coordinates of the at least three points in the virtual coordinate system, wherein the at least three points are preset and not collinear;
obtaining, by imaging a prefabricated registration standard board that comprises three optical marks, and onto which the entity model is mounted, coordinates of the three optical marks in a visual coordinate system, and obtaining a homogeneous matrix according to the coordinates of the three optical marks in the visual coordinate system;
obtaining coordinates of points on the entity model corresponding to the at least three points on the 3D model of the substrate in the visual coordinate system according to coordinates of the points on the entity model corresponding to the at least three points on the 3D model of the substrate in the prefabricated registration standard board and the homogeneous matrix;
obtaining a position and attitude matrix of the entity model in the visual coordinate system according to the coordinates of the points on the entity model corresponding to the at least three points on the 3D model of the substrate in the visual coordinate system;
obtaining a correspondence between the virtual coordinate system and the visual coordinate system according to the position and attitude matrix of the baseline 3D model in the virtual coordinate system and the position and attitude matrix of the entity model in the visual coordinate system; and
providing the correspondence to a navigation device to enable robot-assisted dental implant surgery to be performed on the target tooth.

10. A non-transitory computer readable storage medium, storing computer instructions that, when executed by at least one processor included in a computing device, cause the computing device to carry out steps that include:
obtaining a baseline 3D model of a target tooth to be registered, wherein the baseline 3D model includes (1) a first 3D model of an entity model of the target tooth, and a (2) 3D model of a substrate to which the entity model is attached, wherein the 3D model of the substrate is preset;
performing a live scan of the target tooth to obtain a second 3D model that corresponds to the first 3D model;
utilizing the second 3D model as a reference to register the baseline 3D model with the second 3D model;
obtaining coordinates of at least three points on the 3D model of the substrate in a virtual coordinate system in which the second 3D model is located, and obtaining a position and attitude matrix of the baseline 3D model in the virtual coordinate system according to the coordinates of the at least three points in the virtual coordinate system, wherein the at least three points are preset and not collinear;
obtaining, by imaging a prefabricated registration standard board that comprises three optical marks, and onto which the entity model is mounted, coordinates of the three optical marks in a visual coordinate system, and obtaining a homogeneous matrix according to the coordinates of the three optical marks in the visual coordinate system;
obtaining coordinates of points on the entity model corresponding to the at least three points on the 3D model of the substrate in the visual coordinate system according to coordinates of the points on the entity model corresponding to the at least three points on the 3D model of the substrate in the prefabricated registration standard board and the homogeneous matrix;
obtaining a position and attitude matrix of the entity model in the visual coordinate system according to the coordinates of the points on the entity model corresponding to the at least three points on the 3D model of the substrate in the visual coordinate system;
obtaining a correspondence between the virtual coordinate system and the visual coordinate system according to the position and attitude matrix of the baseline 3D model in the virtual coordinate system and the position and attitude matrix of the entity model in the visual coordinate system; and
providing the correspondence to a navigation device to enable robot-assisted dental implant surgery to be performed on the target tooth.

* * * * *